United States Patent [19]

Reyniers et al.

[11] Patent Number: 5,861,523
[45] Date of Patent: Jan. 19, 1999

[54] METAL CARBOXYLATES

[75] Inventors: Sylvain Leontina Edmond Reyniers, Kapelle-op-den-Bos; Karen S'Jegers, Geel, both of Belgium

[73] Assignee: Exxon Chemical Patents Inc., Houston, Tex.

[21] Appl. No.: 809,663

[22] PCT Filed: Sep. 26, 1995

[86] PCT No.: PCT/EP95/03822

§ 371 Date: May 30, 1997

§ 102(e) Date: May 30, 1997

[87] PCT Pub. No.: WO96/10007

PCT Pub. Date: Apr. 4, 1996

[30] Foreign Application Priority Data

Sep. 29, 1994 [GB] United Kingdom .................. 9419613

[51] Int. Cl.⁶ ................................ C07F 7/00; C04B 9/02

[52] U.S. Cl. ..................... 556/55; 106/14.28; 106/14.36; 106/31.13

[58] Field of Search ........................... 556/55; 106/14.28, 106/14.36, 31.13

[56] References Cited

U.S. PATENT DOCUMENTS 3,036,101 5/1962 Tittle ........................................ 556/55

FOREIGN PATENT DOCUMENTS 0 010 807 A1  5/1980  European Pat. Off. .
0 234 649 A1  9/1987  European Pat. Off. .

*Primary Examiner*—Porfirio Nazario-Gonzalez
*Attorney, Agent, or Firm*—Blossom E. Loo

[57] ABSTRACT

Basic zirconium carboxylates of branched chain aliphatic monocarboxylic acids having 5 to 10 carbon atoms are disclosed. The carboxylates may be used, inter alia, as driers for paints and inks.

16 Claims, No Drawings

METAL CARBOXYLATES

This application was filed as a request for U.S. examination under 35 U.S.C. §371 of International application No. PCT/EP95/03822 filed Sep. 26, 1995.

The invention relates to basic zirconium carboxylates, to a process for the preparation of such carboxylates, and to the use of the carboxylates as, inter alia, driers for paints and inks. The carboxylates may also find use as, for example, lubricant additives, fuel additives, or polymerization catalysts.

The use of metallic soaps, or driers, in drying oil compositions has been known for centuries The soaps accelerate the "drying" of unsaturated oils such as linseed oil or unsaturated synthetic resins such as alkyd resins used as, for example, the base for paints. The metal part of the soap is generally assumed to be the active part of the drier: it is believed that the metal catalyses oxidation and/or polymerization processes in the oil or unsaturated alkyd paint base. In view of this, it is generally desirable that the soap contains as high a proportion of metal as possible.

Among the metallic soaps commonly used as driers for, for example, paints and inks, are carboxylates of cobalt, manganese, calcium, lead, barium and zinc. U.S. Pat. No. 2,739,902 indicates that, under certain conditions, cobalt, manganese, calcium, and lead carboxylates used as driers can be replaced in part (in the case of the cobalt or manganese carboxylates) or entirely (in the case of the calcium and lead carboxylates) by zirconium carboxylates. Advantages said to arise from such replacement are reduction in costs, as compared with the use of cobalt and/or manganese carboxylates alone, or in toxicity, in the case of the lead compounds. The U.S. specification indicates that it is generally the practice to use as small an amount of driers as possible, not only because of economic considerations but also because it is known that a high content of driers in a surface coating is extremely detrimental to the ageing properties of the coating, causing embrittlement, discoloration, and peeling off of the coating film.

The U.S. specification indicates that suitable zirconium compounds are particularly zirconyl naphthenate, 2-ethyl hexanoate, tollate, and linoleate, and, generally, the salts of the zirconyl radical $ZrO^{2+}$ with aliphatic straight or branched chain, saturated or unsaturated, monocarboxylic acids. The specification describes the preparation and use of zirconyl 2-ethyl hexanoate, which is said to exist in a monomeric form, in which the zirconium content of the solid product is 23.17%, or in a dimeric form, in which zirconium atoms are linked via an oxygen atom and in which the zirconium content of the solid product is 35.3%.

A metal soap for use as a drier for, for example, paints and inks, is normally incorporated in the paint or ink in the form of a solution or stable suspension in an organic solvent, such a solution or suspension typically having a metal content, in the case of zirconium carboxylates, of 6 to 12 wt. %.

While it is possible to prepare by direct methods solutions or suspensions of zirconium carboxylates having zirconium contents in the range indicated above, it would be advantageous to be able to prepare by direct methods more concentrated zirconium carboxylates (of acceptable viscosity) which could, if desired, be diluted before use to the desired concentration. The direct preparation of the carboxylates in more concentrated form (that is, preparation without a final concentration step) would make it possible to increase the production capacity of a given reactor, and to supply the zirconium carboxylates in a form in which they contain less solvent, which may in some cases make them easier to handle.

We are aware of commercially available solutions or suspensions of zirconium 2-ethyl hexanoate containing up to 24 weight % of zirconium. Any attempt to remove solvent from such solutions/suspensions, however, results in a highly viscous product, which is not suitable for direct incorporation in a paint or ink formulation. Further, it is not possible to produce directly 2-ethyl hexanoates with a metal content greater than 24 weight % as such products would be too viscous to handle economically when working on a commercial scale. There is a need, therefore, for zirconium carboxylates which are easy to prepare and which can, if desired, be obtained in a liquid form (that is, in solution in or in admixture with an organic liquid) having an acceptable viscosity and containing more than 24 weight % of zirconium. There is also a need for zirconium carboxylates with lower proportions of zirconium, for example, more than 12 weight to 24 weight % of zirconium, which provide an additional or alternative source of zirconium at proportions in that range.

The present invention provides a basic zirconium carboxylate in solution in, or in admixture with, an organic liquid, the carboxylate groups in the basic zirconium carboxylate consisting essentially of groups derivable from at least one branched chain aliphatic monocarboxylic acid which has 5 to 10 carbon atoms (including the carbon atom in the carboxylic group) and in which any branching group (s) on the α-carbon atom contain(s) at most one carbon atom, and the proportion of zirconium being more than 12% by weight, for example, more than 18% by weight, especially more than 24% by weight, based on the weight of the basic zirconium carboxylate and the liquid.

The zirconium carboxylates of the invention are salts of the zirconyl radical, $ZrO^{2+}$. The α-carbon atom in the monocarboxylic acids from which the carboxylates are derivable (and are preferably derived) is the carbon atom adjacent to the carboxyl group. The carboxylates of the invention normally do not contain any metal other than zirconium, apart, possibly, from very small proportions of hafnium which are associated with some sources of zirconium. The presence of other metals may, however be advantageous in some circumstances. Where the presence of another metal is desirable for a particular use, a zirconium carboxylate of the invention is preferably mixed, after its preparation, with a salt, for example, a carboxylate, of the other metal. Examples of particular metals are given later in this specification. Mixed salts are not, however, excluded The carboxylates of the invention may contain minor amounts of carboxylate groups derived from acids which are not branched chain aliphatic C5 to C10 monocarboxylic acids as specified above. Preferably not more than 15 wt %, advantageously not more than 10 wt %, and especially not more than 5 wt %, of the carboxylate groups, based on the total weight of the acids from which the carboxylate groups are derived, are derived from acids other than the specified C5 to C10 acids A basic zirconium carboxylate of the invention may be derived from one, substantially pure, branched chain aliphatic monocarboxylic acid, as specified above, having 5 to 10 carbon atoms. Because commercial processes (e.g., the oxo process carried out on olefin oligomer feedstocks) for the preparation of such acids normally result in a mixture of products, however, the basic zirconium carboxylates will more normally be derived from a mixture consisting essentially of two or more branched chain aliphatic monocarboxylic acids, as specified above, having 5 to 10 carbon atoms. Where at least two branched chain aliphatic C5 to C10 monocarboxylic acids as specified above are present, a first such acid may contain the same number of carbon atoms as a or the second, but be in a different isomeric form from the second, or a first such acid may contain a different number of carbon atoms from a or the second. A mixture of acids containing two or more isomers having a particular number of carbon atoms and at least one acid having a different number of carbon atoms may, of course, also be used. Advantageously the acid, or at least one of the acids, from which any given zirconium carboxylate according to the invention is derived contains 7 to 9 carbon atoms.

The aliphatic chain, including the branching group(s), in the acids from which the basic zirconium carboxylates of the invention are derivable may contain, or be substituted by, one or more atoms or groups which are inert under the conditions to which the acids and carboxylates are subjected during processing and use, but, advantageously, the aliphatic chain, including the branching group(s), is made up of carbon and hydrogen atoms only. Furthermore, the aliphatic chain, including the branching group(s), is preferably saturated.

The acids from which the basic zirconium carboxylates are derivable contain one or more branching groups, which are normally ethyl or methyl groups, on the main aliphatic chain, provided that any branching group(s) on the α-carbon atom contain(s) at most one carbon atom. Subject to this proviso, the branching group(s) may be present at any position on the main chain, although acids containing at least one branching group on a carbon atom other than the α-carbon atom may be preferred in some circumstances. For some purposes, for example, for products to be used in water-based paints, it may be advantageous to have α-branching in addition to non-α-branching.

Examples of acids from which the basic zirconium carboxylates of the invention are derivable are the aliphatic C8, C9 and C10 acids sold by Exxon Chemical under the trade name "Cekanoic", and the branched C7, C8 and C9 neo acids sold by Exxon Chemical, the neo acids being di-α branched, having two methyl groups on the α-carbon atom, and also having branching elsewhere in the chain. Cekanoic C8 acid comprises predominantly C8 non-α branched isomers, while Cekanoic C9 acid is predominantly 3,5,5-trimethyl hexanoic acid. Other acids which may be used include the mixture of C9 isomers known as isononanoic acid.

Mixtures of one or more of the acids, or types of acids, referred to above may of course be used.

As the overbased carboxylates are used without removal of the liquid in which they are dissolved or with which they are mixed, the choice of liquid will normally be dependent in part on the intended end use of the product. Preferred organic liquids for overbased zirconium carboxylates to be used as driers for, for example, paints and inks, are hydrocarbons, especially aromatic, dearomatised and iso-paraffinic hydrocarbons. Especially advantageous liquids for driers are dearomatised hydrocarbons, for example, white spirit.

The zirconium carboxylates of the invention are basic, or overbased, that is to say, the quantity of metal present is greater than that predicted by stoichiometry as being required to react completely with the monocarboxylic acid (s) to give neutral carboxylates of the formula $ZrOAc_2$, where Ac is a carboxylate group. Further, at least part of the excess metal is preferably present in inorganic form. The extent to which a salt is basic or overbased can be expressed in a number of different ways, but in this specification will be expressed as the basicity, that is, the ratio of $ZrO^{2+}$ equivalents to carboxylic acid equivalents. A neutral salt will have a basicity of 1, while a basic or overbased salt will have a basicity of greater than 1. A high basicity is advantageous as this minimizes the weight of any given carboxylic acid required for the introduction of a specified weight of zirconium into, for example, a paint or ink formulation. Basic carboxylates in accordance with the invention may readily be prepared with basicities of 1.25 or more, for example, up to about 1.5 or, in some cases, up to about 1.75.

The precise structure of the basic carboxylates of the invention is unknown, but it is thought to be predominantly micellar, the micelles, which comprise zirconium in inorganic form, for example as zirconyl carbonate, surrounded by zirconyl carboxylate molecules, being in the form of a colloidal solution in the organic liquid. When the carboxylate is used as a drier for, for example, a paint or ink it is incorporated into the paint or ink in liquid form.

The Applicants have surprisingly found that colloidal solutions of the basic zirconium carboxylates of the invention can have an acceptable viscosity even at high zirconium contents, for example, at zirconium contents of 24wt. % or more. The relatively low viscosities of colloidal solutions of carboxylates of the invention having high zirconium contents give rise to a number of advantages, including a saving in production costs (because filtration, which is frequently a problem with overbased salts, is easier and quicker), and better mixing and processability when the carboxylates are used in, for example, paint or ink formulations, including improved filterability if the formulations are to be filtered. A further advantage of the salts of the invention over the corresponding salts of, for example, 2-ethyl hexanoic acid, is the fact that the salts of the invention having a high zirconium content can be obtained directly, without the need for a concentration step, and higher basicities are obtainable with the acids used in accordance with the invention, as compared with 2-ethyl hexanoic acid.

Any suitable process may be used for preparing the basic zirconium carboxylates of the invention. Thus, for example, the carboxylates may be prepared by a process in which a basic zirconium compound is reacted with an acidic gas, preferably carbon dioxide, in an organic medium containing (a) the monocarboxylic acid(s) and a zirconium compound capable of reacting with the acid(s), and/or (b) a zirconium carboxylate obtainable by reaction of the acid(s) and zirconium compound specified in (a). If desired, although this is not preferred, the carboxylate may be provided as a salt of another metal.

Advantageously, however, the basic zirconium carboxylates of the invention are made by a process which comprises reacting zirconyl carbonate and at least one branched chain aliphatic monocarboylic acid from which the carboxylates are derivable, the process being carried out in an liquid medium which is inert under the conditions used in the process and which is advantageously the same as the liquid medium in the final product. The liquid medium advantageously comprises an organic liquid which boils at a temperature above the boiling point of water, for example, a temperature of at least 150° C.

The zirconyl carbonate starting material is normally used in the form of a hydrate and the reaction is advantageously carried out, with mixing, in the presence of the inert organic liquid. Where a hydrate and an organic liquid are used, it is advantageous to carry out the reaction with moderate heating, for example up to a temperature of about 80° C., to facilitate the separation of the liquid reaction medium into an aqueous and an organic phase. It may also be advantageous to allow the reaction mixture to stand for a time, for example, 30 to 60 mins, without further heating, to allow substantially complete separation of the two phases. When phase separation is substantially complete, the aqueous phase can be removed, for example, decanted off. When the carboxylate contains a relatively high proportion of zirconium, separation into two phases may not occur. In this case, the water is removed, where necessary, by heating, for example as described below.

The organic phase remaining after removal of the aqueous phase, where phase separation does occur, will normally still contain some water, for example, up to 30 wt. % of water, based on the weight of the organic phase. It is normally desirable to remove at least some of this residual water, to facilitate the production of a stable, clear product. The water is advantageously removed by heating the organic phase to a temperature significantly above the boiling point of the water, for example, a temperature of 150° C. to 180° C. if operating at normal atmospheric pressure. If necessary, an additional quantity of the organic liquid may be added before removal of water from the organic fraction. After removal of the desired amount of water the product may be filtered, if necessary, preferably at an elevated temperature.

In accordance with the invention, it is possible, especially when the preferred process features referred to above are used, to obtain colloidal solutions of basic zirconium salts of the specified C5 to C10 branched chain aliphatic monocarboxylic acids with a relatively high zirconium content (for example, over 24 wt. %) directly, without the use of a final concentration step to reduce the amount of organic liquid present. If the acid(s) used in accordance with the invention are replaced in whole or in substantial amounts by, for example, 2-ethyl hexanoic acid, attempts to obtain high zirconium contents lead to solid rather than liquid products.

As indicated above, the fact that the present invention makes it possible to prepare zirconium carboxylates containing a high proportion of zirconium has the advantage that the production capacity of a given reactor can be increased. Further, where the carboxylates are of high basicity, less acid is required than for carboxylates of lower basicities. In addition, the invention provides an alternative source of zirconium to zirconium carboxylates previously available and having lower zirconium contents and/or lower basicities.

The basic zirconium carboxylates of the invention can if desired be used in admixture or conjunction with salts, for example, carboxylates, of other metals or mixtures of metals, for example, calcium and cobalt salts, barium and cobalt salts, cobalt and magnesium salts, and cobalt, lead and calcium salts.

As indicated above, the basic zirconium carboxylates of the invention may be used as, inter alia, driers for paints and inks, the term "paints" as used here including clear varnishes with or without colouring materials. Accordingly, the invention also provides a paint or ink which contains an unsaturated compound and a basic zirconium carboxylate in accordance with the invention. One example of an unsaturated compound is linseed oil. Preferably the proportion of the liquid zirconium carboxylate in a paint or ink in accordance with the invention is 0.05 to 0.5 wt. % based on the total composition, including any other constituents. If desired, a composition in accordance with the invention may also comprise another drying agent, for example, a carboxylate of cobalt, manganese, calcium, lead, barium or zinc.

The invention also provides a method for preparing a paint or ink which includes the step of incorporating a basic zirconium carboxylate in accordance with the invention in a formulation which includes an unsaturated compound suitable for paint or ink use. The invention further provides the use of a basic zirconium carboxylate in accordance with the invention as a drier for a paint or ink.

The basic zirconium carboxylates of the invention may also find application as, additives, for example, extreme pressure additives, for lubricating oils. Other possible uses include use of the carboxylates as fuel additives or polymerization catalysts.

Examples 1 to 5 illustrate the invention. Example A is provided by way of comparison.

EXAMPLES 1 to 5

A reactor vessel, equipped with a mechanical stirrer, a condenser, a Dean Stark apparatus, a thermocouple and a heating mantle with a regulator was charged with x parts by weight of hydrated basic zirconium carbonate ($Zr_2O_3CO_3.nH_2O$), y parts by weight of Cekanoic ("CK") C8 acid or neo C8 acid and z parts by weight of the dearomatized hydrocarbon sold by Exxon Chemical Limited under the name Exxsol D40. The temperature was allowed to rise to 40° C. The temperature was then increased to 80° C., with stirring, and maintained at that level for approximately 10 min. The mixture was allowed to stand for 30 mins at 80° C. during which it separated into an aqueous phase and an organic phase. The aqueous phase was carefully decanted off, without prior cooling.

Over the next 30 to 45 mins the temperature of the organic phase was raised to approximately 160° C. for substantially complete elimination of water. The organic phase was then cooled to 100° C. and filtered through a Buchner filter. The viscosity of the filtered and cooled product was then measured.

The proportions of starting materials used are shown in Table 1. The zirconium proportion, basicity and viscosity of the product are shown in Table 2.

TABLE 1

| Example | x (Zr carbonate | y (acid) | z (solvent) |
|---|---|---|---|
| 1 | 380 | 254 CK C8 | 127 |
| 2 | 362 | 253 Neo C8 | 129 |
| 3 | 233 | 148 CK C8 | 32 |
| 4 | 424 | 296 Neo C8 | 64 |
| 5 | 233 | 127 CK C8 | 53 |

TABLE 2

| Example | wt. % Zr | Basicity (acid) | Viscosity cSt |
|---|---|---|---|
| 1 | 24 | 1.5 | 366 at 20° C.* |
| 2 | 24 | 1.5 | 2259 at 20° C.* |
|  |  |  | 468 at 40° C. |
| 3 | 28 | 1.5 | 10281 at 20° C. |
| 4 | 28 | 1.5 | 7037 at 40° C. |
| 5 | 28 | 1.75 | 648 at 20° C. |

*A commercially available zirconium carboxylate having a zirconium content of 24 wt. % and a basicity of 1.25 had a viscosity of approximately 2500 cSt at 20° C. (1 cSt = 1 $mm^2/s$)

Example A (Comparative)

The procedure used in Examples 1 to 5 was repeated using 245 parts by weight of 2-ethyl hexanoic acid, 359 parts by weight of zirconium carbonate, and 84 parts by weight of the dearomatised hydrocarbon. The overbased salt produced had a zirconium content of 24 wt. % and a basicity of 1.5. When cooled to 100° C., the mixture became solid.

We claim:

1. A basic zirconium carboxylate in solution in, or in admixture with, an organic liquid, the carboxylate groups in the basic zirconium carboxylate consisting essentially of groups derivable from at least one branched chain aliphatic monocarboxylic acid which has 5 to 10 carbon atoms and in which any branching group(s) on the α-carbon atom contain(s) at most one carbon atom, and the proportion of zirconium being more than 12% by weight, based on the weight of the basic zirconium carboxylate and the liquid.

2. A zirconium carboxylate of claim 1, wherein the carboxylate groups are derivable from at least two acids having the same number of carbon atoms.

3. A zirconium carboxylate of claim 1, wherein the carboxylate groups are derivable from at least two acids having different numbers of carbon atoms.

4. A zirconium carboxylate as claimed in claim 1, wherein, in at least one acid from which the carboxylic groups are derived, the aliphatic chain, including any branching groups, is made up of carbon and hydrogen atoms only, and is saturated.

5. A zirconium carboxylate as claimed in claim 1, wherein, wherein, in at least one acid from which the carboxylic groups are derived, the one or more branching group is a methyl group or, in the case of a branching group on a carbon atom other than the α-carbon atom, an ethyl group.

6. A zirconium carboxylate as claimed in claim 1, wherein, in at least one acid from which the carboxylate groups are derived, there is at least one branching group on a carbon atom other than the α-carbon atom.

7. A zirconium carboxylate as claimed in claim 6, wherein the said one acid also has at least one methyl group on the α-carbon atom.

8. A zirconium carboxylate as claimed in claim 1, wherein said at least one acid from which the carboxylate groups are derived contains 7 to 9 carbon atoms.

9. A zirconium carboxylate as claimed in claim 1, wherein the carboxylate groups consist essentially of groups derivable from a mixture of acids each having 8 carbon atoms and being branched predominantly in non-α positions.

10. A zirconium carboxylate as claimed in claim 1, wherein the proportion of zirconium is more than 18% by weight, based on the weight of the basic zirconium carboxylate and the liquid.

11. A zirconium carboxylate as claimed in claim 10, wherein the said proportion is at least 24% by weight.

12. A zirconium carboxylate as claimed in claim 1, which is in the form of a colloidal solution in the liquid.

13. A process for preparing a basic zirconium carboxylate as claimed in claim 1, which comprises reacting zirconyl carbonate and at least one monocarboxylic acid as specified in claim 1, the reaction being carried out in an inert liquid medium.

14. A paint or ink comprising an unsaturated compound and a zirconium carboxylate of claim 1.

15. A paint or ink of claim 14 wherein the proportion of liquid zirconium carboxylate is 0.05 to 0.5 wt. % based on the total composition including any other constituents.

16. A paint or ink of claim 14 which also contains a carboxylate of cobalt, manganese, calcium, lead, barium, or zinc.

* * * * *